United States Patent [19]

King et al.

[11] Patent Number: 5,401,378

[45] Date of Patent: Mar. 28, 1995

[54] IONIC RESERVOIR AT ELECTRODE SURFACE

[75] Inventors: Lionel G. King, Sydney; Burkhard Raguse, Sydney; Bruce A. Cornell, Sydney; Ronald J. Pace, Canberra, all of Australia

[73] Assignee: Australian Membrane & Biotechnology Research Institute, North Ryde, Australia

[21] Appl. No.: 119,166

[22] PCT Filed: Mar. 27, 1992

[86] PCT No.: PCT/AU92/00132

§ 371 Date: Sep. 21, 1993

§ 102(e) Date: Sep. 21, 1993

[87] PCT Pub. No.: WO92/17788

PCT Pub. Date: Oct. 15, 1992

[30] Foreign Application Priority Data

Mar. 27, 1991 [AU] Australia .............................. PK5324
Dec. 3, 1991 [AU] Australia .............................. PK9827

[51] Int. Cl.[6] ............................................. G01N 27/26
[52] U.S. Cl. .................................... 204/418; 204/403; 204/153.12; 204/153.1; 435/817; 435/291
[58] Field of Search ................ 204/153.1, 403, 418, 204/153.12; 435/291, 817

[56] References Cited

U.S. PATENT DOCUMENTS

| | | | |
|---|---|---|---|
| 4,490,216 | 12/1984 | McConnell | 204/403 |
| 4,637,861 | 1/1987 | Krull et al. | 204/418 |
| 4,661,235 | 4/1987 | Krull et al. | 204/418 |
| 4,758,325 | 7/1988 | Kanno et al. | 204/418 |
| 4,822,566 | 4/1989 | Newman | 435/817 |
| 4,973,394 | 11/1990 | Ross et al. | 204/418 |
| 5,204,239 | 4/1993 | Gitler et al. | 435/817 |
| 5,234,566 | 8/1993 | Osman et al. | 204/418 |

FOREIGN PATENT DOCUMENTS

| | | |
|---|---|---|
| 64933/74 | 7/1975 | Australia . |
| AU-A-40123/85 | 3/1984 | Australia . |
| AU-B-21279/88 | 7/1988 | Australia . |
| AU-B-40787/89 | 8/1989 | Australia . |
| AU-B-50334/90 | 1/1990 | Australia . |
| AU-A-69245/91 | 7/1991 | Australia . |
| 0261887 | 3/1988 | European Pat. Off. . |

OTHER PUBLICATIONS

A. Laschewsky et al. "Self-organization of polymeric . . . " J. Am. Chem. Soc. 1987, 109, pp. 788–796, no month available.

C. D. Bain et al. "Formation of Monolayer . . . " J Am Chem Soc 1989, 111, pp. 321–335, no month available.

M. D. Porter et al. "Spontaneously Organized Molecular . . . " J Am Chem Soc, 1987, 109, pp. 3559–3568, no month available.

T. Diem et al. "Spontaneous assembly . . . " J Am Chem Soc, 1986, 108, pp. 6094–6095, no month available.

F. S. Ligler et al. "A recepter-based biosensor . . . " Molecular Electronics Science & Technology, Feb. 19–24, 1989, no month available.

U. J. Krull et al. "Lipid membrane technology . . . " Trends Anal Chem 3 (3) 1984) VII–X, no month available.

C. J. Miller et al. "Microporous aluminum . . . " J Phys Chem, 1988, 92, pp. 1928–1936, no month available.

R. Merkel et al. "Molecular friction and epitactic . . . " J Phys Chem, 50 (1989), pp. 1535–1555, no month available.

P. Yager. "Functional reconstitution . . . " Biosensors 2 (1986) pp. 363–373, no month available.

*Primary Examiner*—John Niebling
*Assistant Examiner*—Bruce F. Bell
*Attorney, Agent, or Firm*—Nixon & Vanderhye

[57] ABSTRACT

The present invention relates to electrode membrane combinations for use in biosensors. The membrane is attached to the electrode by means of a linker molecule in a manner such that a hydrophilic space is provided between the membrane and the electrode. The linker molecule comprises within the same molecule a hydrophobic region which constitutes at least a proportion of the amphiphilic molecules making up the membrane or is attached to or is embedded in the membrane, an attachment region attached to the electrode and a hydrophilic region intermediate said hydrophobic and attachment regions. The hydrophilic region spans the space between the membrane and the electrode.

29 Claims, 5 Drawing Sheets

IONIC RESERVOIR AT ELECTRODE SURFACE

FIELD OF THE INVENTION

The present invention relates to electrode membrane combinations for use in biosensors. In addition, the present invention relates to methods for the production of such electrode membrane combinations and the use of biosensors incorporating such electrode membrane combinations in the detection of analytes. The present invention also relates to novel compounds used in the electrode membrane combinations.

BACKGROUND OF THE INVENTION

Biosensors comprising membranes incorporating gated ion channels have been disclosed in International Patent Application Nos. WO89/01159 and WO90/08783. As is disclosed in these applications, suitably modified receptor molecules may be caused to co-disperse with amphiphilic molecules and produce membranes with altered surface binding properties, which are useful in the production of biosensor receptor surfaces of high-binding ability and high-binding specificities. It is also disclosed that ion channels such as polypeptide ionophores may be co-dispersed with amphiphilic molecules, thereby forming membranes with altered properties in relation to the permeability of ions. There is also disclosure in these applications of various methods of gating these ion channels such that in response to the binding of an analyte the conductivity of the membrane is altered.

DESCRIPTION OF THE INVENTION

The present inventors have now determined that the stability and ion flux properties of such membranes formed on solid substrates can be greatly improved by chemisorbing or covalently attaching an array of amphiphilic compounds onto an electrode surface such that a space is formed between the electrode and the membrane.

Prior art has taught the use of such concepts as hydrogels or porous silicon as reservoirs onto which bilayer membranes may be formed. These processes are difficult to reproduce and to date no reliably and reproducibly functioning examples have been cited in the art. The present invention differs from the prior art in that it consists of a single molecule that contains within it membrane compatible hydrophobic groups, ion compatible hydrophilic groups and groups capable of chemisorbing or covalently attaching onto an electrode surface linked in such a way so as to produce functioning amphiphilic membrane/reservoir/electrode assemblies. This invention also allows for a much simpler manufacturing process yielding far more controllable, reproducible, and stable bilayer and monolayer membranes that allow the incorporation of functioning ionophores or ion channels.

Accordingly, in a first aspect, the present invention consists in an electrode membrane combination comprising an electrode and a membrane comprising a closely packed array of amphiphilic molecules and a plurality of ionophores the membrane being connected to the electrode by means of a linker molecule(s) in a manner such that a hydrophilic space is provided between the membrane and the electrode, the space being sufficient to allow the flux of ions through the ionophores, the linker molecule comprising within the same molecule a hydrophobic region which constitutes at least a proportion of the amphiphilic molecules making up the membrane or is attached to or is embedded in the membrane, an attachment region attached to the electrode and a hydrophilic region intermediate said hydrophobic and attachment regions and spanning said space between the membrane and the electrode.

In a preferred embodiment of the invention the distance between the membrane and the electrode is in the range 10 to 1000 Å and more preferably is in the range 15-100 Å.

In a further preferred embodiment of the invention the hydrophobic region of the linker molecule constitutes at least a proportion of the amphiphilic molecules making up the membrane.

In a preferred form of the invention when the membrane is a monolayer all the amphiphilic molecules are the hydrophobic region of the linker molecules, and in the situation where the membrane is a bilayer all the amphiphilic molecules making up the layer adjacent the electrode are the hydrophobic region of the linker molecules. The hydrophobic region may either span half the membrane or may span the full membrane. Mixtures of half membrane spanning and full membrane spanning components may also be used. In the situation where the membrane is a monolayer the hydrophobic region will typically span the full membrane.

Effective linker molecules can be achieved using hydrophobic regions containing any of a wide variety of saturated or unsaturated hydrocarbon chains, typically of carbon chain lengths 10-40 carbon atoms. These hydrophobic groups may be joined to the hydrophilic reservoir group either singly or as double or triple chain components joined via commonly utilised groups in lipid synthesis such as glycerol, glutamic acid or triethanolamine.

In a further preferred embodiment the hydrophobic region consists of dioleyl glutamate.

In a further preferred embodiment the hydrophobic region consists of di(X) glutamate where X=an alkyl chain between 12-20 carbon atoms in length.

In a further preferred embodiment the hydrophobic region consists of glycerol didodecanoate, glycerol ditetradecanoate, glycerol dihexadecanoate, glycerol dioctadecanoate or glycerol dioleate.

In a further preferred embodiment the hydrophobic region consists of an archaebacterial lipid or a synthetic membrane spanning archaebacterial lipid mimic.

In a further preferred embodiment the hydrophobic region contains groups such as styrene or acetylenic groups or other commonly polymerisable groups that may be polymerised.

In a further preferred embodiment the hydrophobic region is a membrane compatible ion channel such as gramicidin or one of its derivatives.

It has been shown that the use of such linker molecules embedded into the membrane increases the stability of the membrane.

In a further embodiment of the present invention the attachment region of the linker molecule is attached to the electrode surface by chemisorption. In a situation where the electrode is formed of a transition metal such as gold, platinum, palladium or silver, it is preferred that the attachment region includes thiol, disulphide, sulphide, thione, xanthate, phosphine or isonitrile groups.

In a further preferred embodiment the electrode is formed of gold, silver, platinum or palladium and the attachment region includes either a thiol or a disulfide group, the linker molecule being attached to the electrode by chemisorption.

In a an alternate embodiment where the electrode is formed such that a hydroxylated surface is formed on the electrode, it is preferred that the attachment region includes silyl groups such as silyl-alkoxy or silyl chloride groups. The hydroxylated electrode surface may be a prepared by a number of techniques known to someone skilled in the art and may consist of oxidised silicon or oxidised metals such as tin, platinum, iridium.

In yet a further preferred embodiment the electrode is formed of oxidised silicon, tin, platinum or iridium and the attachment region includes silyl groups, the linker molecule being attached to the electrode by covalent attachment.

The hydrophilic region of the linker molecule is preferably a long chain hydrophilic compound. The hydrophilic region of the linker molecule may be composed of oligo/poly ethers, oligo/poly peptides, oligo/poly amides, oligo/poly amines, oligo/poly esters, oligo/poly saccharides, polyols, multiple charged groups (positive and/or negative), electroactive species or combinations thereof. The main requirement of the hydrophilic region of the linker molecule is that it allows the diffusion of ions through the ionophores provided in the membrane. This is achieved by the placement of suitable ion and/or water binding sites along or within the length of the long chain that makes up the reservoir region.

In a preferred embodiment of the invention the hydrophilic region consists of an oligoethylene oxide group. The oligoethylene oxide group may consist of four to twenty ethylene oxide units.

In a further preferred embodiment the hydrophilic region consists of a subunit of tetraethylene glycol attached to succinic acid. This tetraethylene glycol/succinic acid subunit may be repeated 1-4 times.

In a further preferred embodiment the hydrophilic region is formed by group transfer or anionic polymerisation of suitable monomers.

In a further preferred embodiment the hydrophilic region consists of mercaptoethanol, succinic acid, 1,4-diesterified 1,2,3,4-butanetetraol and succinic acid subunits. The succinic acid/1,4-diesterified 1,2,3,4-butanetetraol may be repeated 1-4 times.

In yet another embodiment of the present invention the ionophores are gated such that in the presence of an analyte the conductance of the membrane is altered.

In a preferred form of the present invention the ionophore is selected from the group consisting of gramicidin, valinomycin and crown ether analogues.

As will become clear from the following examples when the ionophore is valinomycin or a crown ether analogue or an ion selective ion channel the electrode membrane combination of the present invention will function as an ion selective electrode.

Accordingly, in a second aspect, the present invention consists in an ion selective electrode comprising an electrode and a membrane comprising a closely packed array of amphiphilic molecules and a plurality of ionophores selected from the group consisting of valinomycin, crown ether analogues and ion selective ion channels, the membrane being connected to the electrode by means of a linker molecule(s) in a manner such that a hydrophilic space is provided between the membrane and the electrode, the space being sufficient to allow the flux of ions through the ionophores, the linker molecule comprising within the same molecule a hydrophobic region which constitutes at least a proportion of the amphiphilic molecules making up the membrane or is attached to or is embedded in the membrane, an attachment region attached to the electrode and a hydrophilic region intermediate said hydrophobic and attachment regions and spanning said space between the membrane and the electrode.

Further, where the ionophore is gramicidin the electrode membrane combination can be used to detect the presence of small neutral organic molecules such as ethanol. This is due to the fact that such small neutral organic molecules change the structure and physical properties of the membrane by either swelling the membrane or changing the surface tension of the membrane and hence influence the conduction of the ion channel. Accordingly, the electrode membrane combination of the present invention may also be used as a chemical sensing membrane.

As discussed above various methods of gating ionophores are disclosed in International Patent Application Nos. WO89/01159 and WO 90/0873. As used herein the term "gated ionophore" is intended to convey an ionophore in which the capacity of ions to pass through the ionophore varies depending on the presence or absence of an analyte.

In a third aspect the present invention consists in a method of assaying for the presence of an analyte in a sample comprising contacting the electrode membrane combination of the first aspect of the present invention in which the ionophores are gated with the sample and measuring the conductivity of the membrane, a change in conductivity indicating the presence of the analyte in the sample.

In a fourth aspect the present invention consists in a method of producing an electrode membrane combination comprising:

(1) Forming a solution containing linker molecules comprising attachment regions, hydrophilic regions and hydrophobic regions which either self-assemble to form a membrane monolayer including a plurality of ionophores or which are attached to or which are embedded in a membrane monolayer composed of self-assembling amphiphilic molecules and a plurality of ionophores;

(2) contacting the electrode with the solution, the composition of the electrode and the attachment regions being selected such that the attachment regions chemisorb to the electrode; and (3) Rinsing the coated electrode.

In a preferred embodiment of this aspect of the present invention the coated electrode is soaked in trifluoroethanol or similar solution for about one week or is subjected to treatment at 60° C. for one hour in trifluoroethanol or a similar solution.

In a further preferred embodiment of the present invention a second membrane layer is assembled onto the coated electrode by contacting the coated electrode by contacting the coated electrode with a solution of lipid containing an alkane of length $C_8$–$C_{16}$ or squalene in a carrier solvent which allows partitioning of the alkane/lipid and which is water soluble.

In yet a further preferred embodiment of this aspect of the present invention the alkane is selected from the group consisting of N-decane, hexadecane and squalene.

The alkane is used to seal ion leakage paths in the membrane while the carrier solvent disperses into an aqueous solution leaving a residual lipid monolayer over the monolayer coating the electrode thus forming a bilayer membrane. It is preferred that the carrier solvent is sufficiently non-volatile that the membrane does not dry out during deposition and is water soluble to allow the carrier solvent to be removed from the membrane by immersion and/or rinsing in an aqueous solution. A typical solution may contain 50 mg/ml glycerol monooleate in dioxane with addition of 2% hexadecane, in this example dioxane is the carrier solvent. Such a membrane can be formed by applying one micro-liter of the solution to a 1 mm diameter gold electrode which has a monolayer coating spaced from the electrode by the linker molecule which has been freshly deposited from a solvent such as ethanol or N-decane. After application of the second layer the electrode assembly is immersed in a solution of water or saline. If required the water or solvent can be exchanged without damaging the membrane as long as the membrane does not pass through the air/water interface, in order to remove traces of the carrier solvent.

In a fifth aspect the present invention consists in a linker molecule for use in attaching a membrane to an electrode and providing a space between the membrane and the electrode, the linker molecule comprising, within the same molecule:

(1) A hydrophobic region selected from the group consisting of dioleyl glutamate, di(X) glutamate where X is an alkyl chain between 12-20 carbon atoms in length, glycerol didodecanoate, glycerol ditetradecanoate, glycerol dihexadecanoate, glycerol dioctadecanoate, glycerol dioleate, archaebacterial lipid, synthetic membranes spanning archaebacterial lipid mimics and membrane compatible ion channels;

(2) A hydrophilic region selected from the group consisting of oligo/poly ethers, oligo/poly peptides, oligo/poly amides, oligo/poly amines, oligo/poly esters, oligo/poly saccharides, polyols, multiple charged groups, electroactive species and combinations thereof; and (3) An attachment region selected from the group consisting of thiol, disulphide, sulphide, thione, xanthate, phosphine, isonitrile and silyl groups. In a preferred embodiment of this aspect of the present invention the hydrophobic region is gramicidin.

In yet a further preferred embodiment of the present invention the hydrophilic region of the linker molecule consists of an oligo ethylene oxide group preferably consisting of 4 to 20 ethylene oxide units.

In yet a further preferred embodiment of the present invention the hydrophilic region of the linker molecule consists of 1-4 subunits of tetraethylene glycol attached to succinic acid.

In yet a further preferred embodiment of the present invention the hydrophilic region of the linker molecule consists of mecapto ethanol, and 1 to 4 succinic acids/1,4 diesterified, 1,2,3,4-butanetetraol subunits.

BRIEF DESCRIPTION OF THE DRAWINGS

In order that the nature of the present invention may be more clearly understood, preferred forms thereof will now be described with reference to the following examples and figures in which.

EXAMPLES

Example 1

Figure 1:
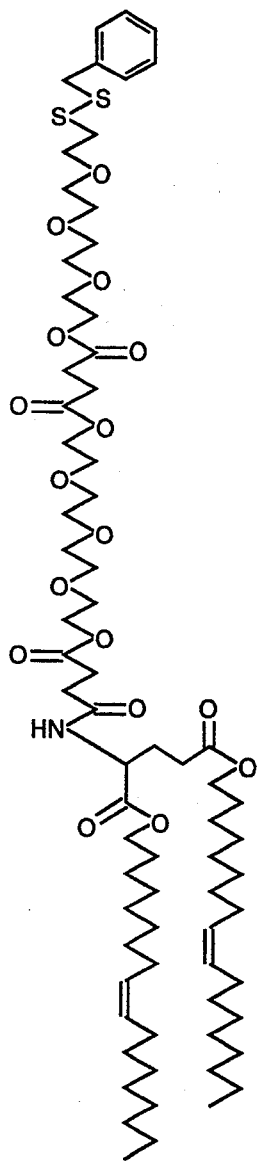
FIG. 1 shows linker molecule 1 which comprises a benzyl disulphide attachment region, a hydrophilic region composed, in sequence of tetraethylene glycol, succinic, tetraethylene glycol and succinic acid subgroups and a hydrophobic region of dioleylglutamate.
Figure 2:
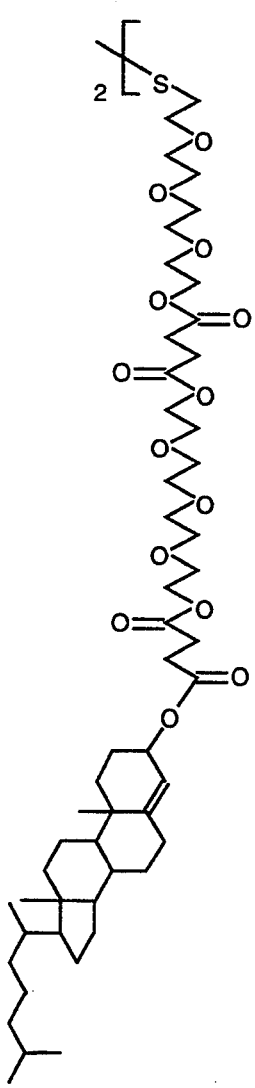
FIG. 2 shows linker molecule 2 which comprises a symmetrical disulphide attachment region, a hydrophilic region composed, in sequence of tetraethylene glycol, succinic acid, tetraethylene glycol and succinic acid subgroups and a hydrophobic region composed of cholesterol.
Figure 7:
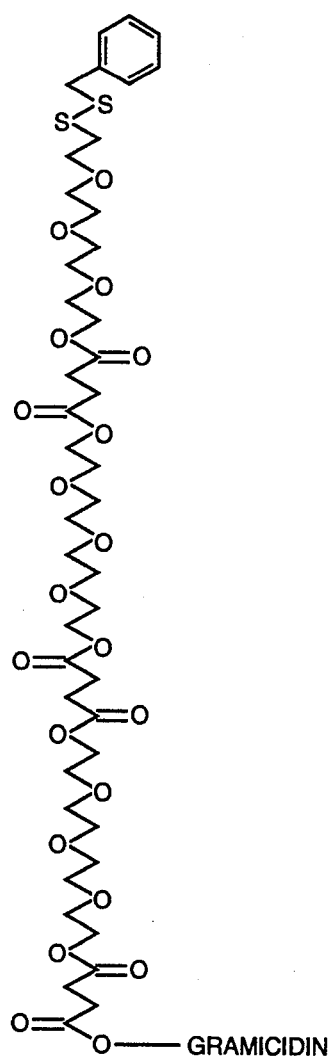
FIG. 7 shows linker molecule 7 which comprises a benzyl disulfide attachment region, a hydrophilic region composed, in sequence, of tetraethylene glycol, succinic acid, tetraethylene glycol, succinic acid, tetraethylene glycol, succinic acid and a hydrophobic region of gramicidin.
Figure 5:
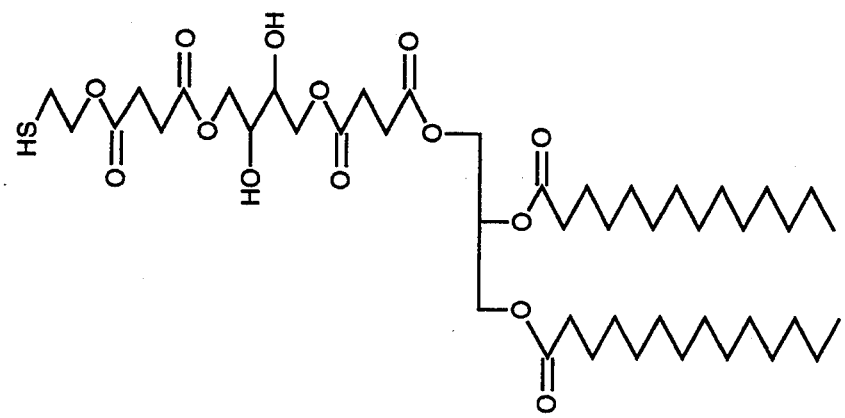
FIG. 5 shows linker molecule 5 which comprises a thiol or disulphide attachment region, a hydrophilic region composed, in sequence, of mercaptoethanol, succinic acid, 1,4-diesterified 1,2,3,4-butanetetraol and succinic acid subunits and a hydrophobic region of 1,2-glycerol ditetradecanoate.
Figure 4:
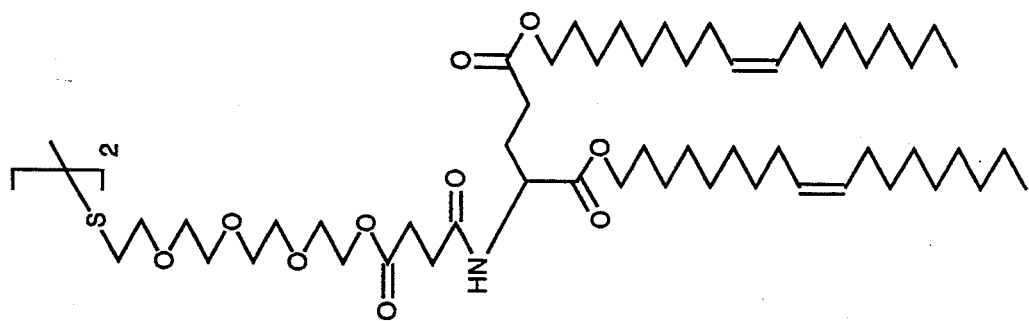
FIG. 4 shows linker molecule 4 which comprises a symmetrical disulphide attachment region, a hydrophilic region comprising, in sequence, of tetraethylene glycol and succinic acid subgroups and a hydrophobic region composed of dioleylglutamate.
Figure 3:
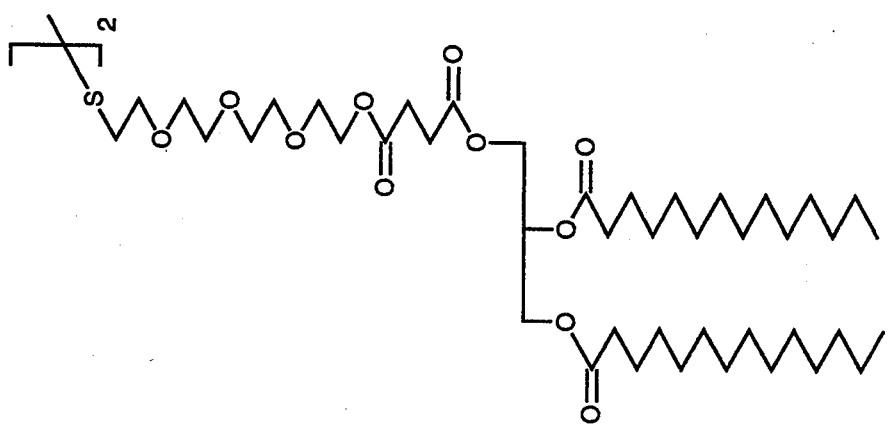
FIG. 3 shows linker molecule 3 which comprises a symmetrical disulphide attachment region, a hydrophilic region composed, in sequence, of tetraethylene glycol and succinic acid subgroups and a hydrophobic region composed of 1,2-glycerol ditetradecanoate.
Figure 6:
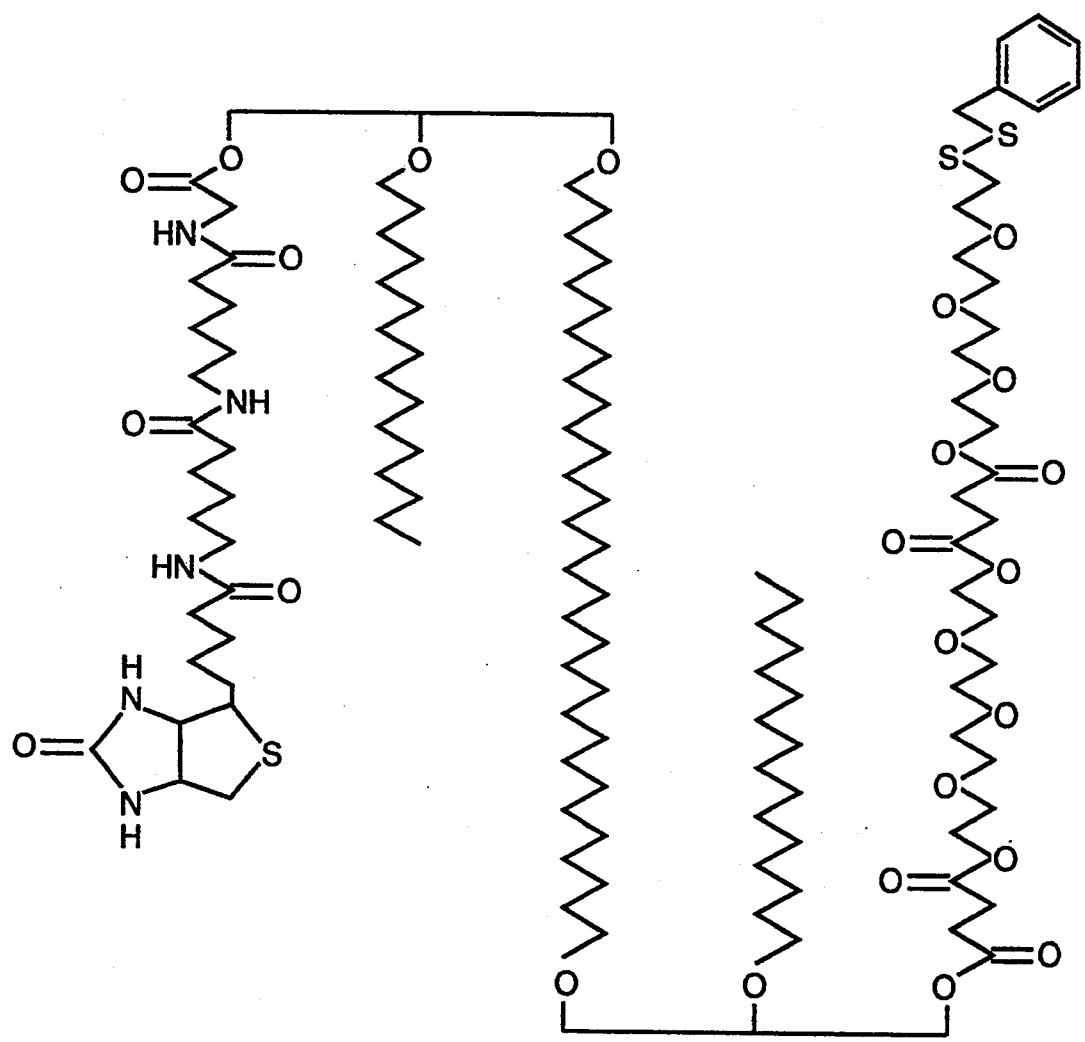
FIG. 6 shows linker molecule 6 which comprises a benzyl disulphide attachment region, a hydrophilic region composed, in sequence, of tetraethylene glycol, succinic acid, tetraethylene glycols, succinic acid, and a hydrophobic region of 1,1' dotriacontamethylenebis (2-hexadecyl-sn-glycerol and a head group consisting of glycine, 1,6-amino caproic acid, 1,6-amino caproic acid and biotin.

Details of linker chemistry synthesis Experimental: Synthesis of linker molecule 1
1) compound 8
10-(4-methyl phenylsulfonyl)-3,6,8,12-tectraoxadecanol
o-Toluenesulfonyl chloride (12.5 g) was added slowly to a solution of tetraethylene glycol (27 g) at 0–5 C. The mixture was left for 24 h at 0–5 C. The mixture was then poured onto hydrochloric acid (2M, 250 ml), and extracted with dichloromethane. The dichloromethane was washed with further hydrochloric acid, dried and evaporated. The residue was chromatographed (silica, ethyl acetate eluent) to give compound 8 (13.6 g).
2) compound 9
10-Mercapto-3,6,9-trioxadecanol Compound 8 (13.6 g) and thiourea (3.1 g) were mixed and refluxed in ethanol (100 ml) for 24H. Sodium hydroxide (4.1 g) in water (5 ml) and ethanol (50 ml) was added to the solution and the mixture was refluxed 2.5 h under nitrogen. The solution was acidified with hydrochloric acid to pH 2 and evaporated. The residue was filtered through silica (10% ethanol/ethyl acetate eluent) to give compound 9 (6.5 g).

3) compound 10
14-Phenyl-12, 13-dithia-3,6,9-trioxatetradecanol

To a mixture of N-chlorosuccinimide (2.16 g) in dry toluene (25 ml) was added benzyl thiol (2.0 g) over 2 minutes. The mixture was stirred a further 10 minutes and then added to a solution of compound 9 (3.4 g) in dry dichloromethane (30 ml). After stirring for an additional 10 minutes the mixture was partitioned between water (100 ml) and dichloromethane (50 ml). The dichloromethane extract was separated, dried, evaporated and the residue was chromatographed (silica, 3% ethanol/dichloromethane) to yield compound 10 (2.9 g).

4) compound 11
4-Oxo-19-phenyl-17,18-dithia-5,8,11,14-tetraoxanonadecanoic acid

A solution of compound 10 (3.1 g) and succinic anhydride (1.5 g) was mixed in pyridine (20 ml) and stirred at room temperature for 18 h. The mixture was poured onto hydrochloric acid (1M, 300 ml, 0° C.), extracted dichloromethane (3×40 ml). The dichloromethane extracts were washed with water (2×200 ml), dried and evaporated to give compound 11 (3.8 g).

5) compound 12
13,16-Dioxo-31-phenyl-29,30-dithia-3,6,9,12,17,20,23, 26-octaoxauntricontanol Compound 11 (0.8 g), dry tetraethylene glycol (2.0 g), dimethylaminopyridine (0.05 g) and dicyclohexyldiimide (0.45 g) were mixed in dichloromethane (10 ml) and stirred for 12 h at room temperature. The mixture was filtered, partitioned between dichloromethane (30 ml) and water (70 ml), separated and the dichloromethane extract was dried and evaporated. The residue was chromatographed (silica, ethyl acetate eluent) to yield compound 12 (0.373 g).

6) compound 13
4,18,21-Trioxo-36-phenyl-34,35-dithia-5,8,11,14,17,22, 25,28,31-nonaoxahexatricontanoic acid Compound 12 (0.314 g), dimethylaminopyridine (0.05 g) and succinic anhydride were dissolved in dichloromethane (10 ml) and refluxed for 48 h. Excess dichloromethane was evaporated and the residue was chromatographed (silica, ethyl acetate eluent) to give compound 13 (0.336 g).

7) compound 14
21-(N-4',4''-Dimethyl-2'-oxo-3'-oxabutylamine)-20,24-dioxo-19,25-dioxatriconta (Z,Z)-9,34-diene To a solution of N-Boc glutamic acid (2.5 g), oleyl alcohol (6.8 g) dimethylaminopyridine (0.1 g) in dry dichloromethane (75 ml) was added dicyclohexyldiimide (5.2 g). The mixture as stirred for 48 h, filtered and the filtrate evaporated. The crude product was chromatographed (silica, hexane/ethyl acetate eluent, 9:1) to give compound 14 (5.5 g).

8) compound 15
21-Amino-20,24-dioxo-19,25-dioxatritetraconta-(Z,Z)-9,34-diene

Compound 14 (3.33 g) was dissolved in dry dichloromethane (100 ml). Dry hydrochloric acid gas was bubbled through the solution for 25 minutes, followed by nitrogen gas for 50 minutes. The dichloromethane solution was washed with potassium carbonate solution (5%, 200 ml), dried and evaporated. The residue was chromatographed (silica, ethyl acetate eluent) to give compound 15 (1.1 g).

9) compound 1
23-(20'-Oxo-19'-oxaeicosa-(Z)-9'-ene)-70-phenyl-20,25,28,42,45-pentaoxo-24-aza-19,29,32,35,38,41,46,47,52,55-decaoxa-58,59-dithiahexaconta-(Z)-9-ene Compound 15 (0.275 g), compound 13 (0.277 g), dimethylaminopyridine (0.02 g) and dicyclohexyldiimide (0.114 g) was dissolved in dry dichloromethane (20 ml) and stirred for 48 h. The mixture was filtered, washed potassium carbonate solution (5%, 20 ml), dried and evaporated. The residue was chromatographed (silica, ethyl acetate/hexane eluent 70:30) to give compound 1 (0.266 g).

PREPARATION OF LINKER MOLECULE OF FIG. 4

10) compound 16
23-(20'-Oxo-19'-oxaeicosa-(Z)-9'-ene)-43-phenyl-20,25,28-trioxo-24-aza-19,29,32,35,38-pentaoxa-41,42-dithiatritetraconta-(Z)-9-ene Compound 15 (0.5 g), compound 11 (0.332 g), dimethylaminopyridine (0.02 g) and diclohexylcarbodiimide (0.16 g) were mixed in dichloromethane (10 ml) and stirred for 18 h. The mixture as filtered and evaporated. The residue was chromatographed (silica, ethyl acetate/hexane, 30:70) to give compound 16 (0.53 g).

11) compound 17
23-(20'-Oxo-19'-oxaeicosa-(Z)-9'-ene)-20,25,28-trioxo-24-aza-19,29,32,35,38-pentaoxa-41-thiauntetraconta-(Z)-9-ene Compound 16 (0.53 g) in ethanol/water (9.1) was treated with tributyl phosphine (1 ml) and stirred for 30 minutes. The reaction mixture was partitioned between dichloromethane (100 ml) and water (100 ml), separated and the dichloromethane extract was dried and evaporated. The residue was chromatographed (silica, ethyl acetate/hexane eluent, 1:1) to give compound 17 (0.388 g).

12) compound 4
23,60-Bis(20'-oxo-19'-oxaeicosa-(Z)-9'-ene)-20,25,55,58,63-pentaoxo-24,59-diaza-19,29,32,35,38,45,48,51,54,64-decaoxa- 41,42-dithiatrioctaconta-(Z,Z)-9,73-diene To a solution of compound 17 (0.25 g) and triethyl amine (0.2 ml) in dichloromethane (10 ml) was added one equivalent of iodine. The mixture was then washed with water (30 ml), dried and evaporated. The residue was chromatographed (silica, ethyl acetate/hexane eluent, 65:45) to give compound 4 (0.164 g).

13) compound 18
38-Phenyl-17-(2'oxo-1'-oxatetradecane)-14,20,23-trioxo-15,19,24,27,30,33-hexaocta-36,37-dithiaoctatricontane Glycerol-1,2-ditetradecanoate (0.59 g), compound 11 (0.5 g), dimethylamino pyridine (0.05 g), and dicyclohexylcarbodiimide (0.263 g) were mixed and stirred in dichloromethane (20 ml) for 18 h. The mixture was filtered, the filtrate evaporated and then chromatographed (silica, ethyl acetate/dichloromethane eluent, (1:9)) to give compound 18 (0.345 g). 14) compound 19
17-(2'-Oxo-1-oxatetradecane)-14,20,23-trioxo-36-thia-15,19,24,27,30,33-hexaoxahexatricontane Compound 18 (0.845 g) was treated in analogous manner to compound 16 with tributyl phosphine (1 ml) to give compound 19 (0.41 g).

15) compound 3

17,56-Bis(2′oxo-1′-oxatetradecane)-14,20,23,50,53,59-hexaoxo-15,19,24,27,30,33,40,43,46,49,54,58-dedecyloxa-36,37-dithiadoheptatricontane Compound 19 (0.2 g) was treated in analogous manner to compound 17 with triethylamine (0.2 ml) and iodine to give compound 3 (0.18 g).

PREPARATION OF LINKER MOLECULE OF FIG. 6

16) compound 20

18,55-Bis(hydroxymethyl)-17,20,53,56-tetraoxadoheptatricontane

The diol (20) was prepared according to the method of Yamuauchi et al, *Biochimica* and *Biophysica ACTA*, 1003, (1989), 151–160.

17) compound 21

18-(8′,8″-Dimethyl-3′,6′-dioxo-5′ aza-2′,7′-dioxanonane)-55-hydroxymethyl-17,20,53,56-tetraoxadoheptacontane A stirred solution of compound 20 in dry dichloromethane (c. 10 mg/ml) was treated with one equivalent of dicylcohexylcarbodiimide, a catalytic quantity of dimethylaminopyridine and one equivalent of N-(t-butyloxycarbonyl)-glycine. The reaction mixture was refluxed for 0.5 h under nitrogen and then stirred at room temperature overnight. The crude reaction mixture was chromatographed (silica, ethyl acetate/hexane eluent, 25:75) to give compound 21 in 48% yield.

18) compound 22

18-(3′-Oxo-5′-aza-2′-oxapentane)-55-hydroxymethyl-17,20,53,56-tetraoxadoheptacontane Compound 21 was treated with freshly distilled trifluoroacetic acid for ten minutes. Excess trifluoroacetic acid was removed in vacuo and the residue was dried by repeated azeotropic distillation with toluene. The residue was then dried for a further 1 h in vacuo to give compound 22 in essentially quantitative yield.

19) compound 23

18-(19′-N-Biotin-3′,6′,13′-trioxo-5′,12′,19′-triaza-2′-oxanonadecane)-55-hydroxymethyl-17,20,53,56-tetraoxadoheptacontane Compound 22 was dissolved in dichloromethane (c. 20 mg/ml) and one equivalent of triethylamine was added. Methanol (c. 50 mg/ml) was then added followed by biotin-XX-N-hydroxysuccinimide (Calbiochem, 1.5 equivalents) and the reaction mixture was stirred at room temperature for 36 h. The solvent was evaporated and the residue was chromatographed (silica, 20–50% ethyl acetate/hexane gradient elution) to give compound 23 in 30% yield.

20) compound 24

58-N-Biotin-22,39-bis(1′-oxaheptadecane)-1-phenyl-16,19,42,45,52-pentaoxo-45,51,58-triaza-6,9,12,15,20,24,37,41-octaoxa-2,3-dithiaoctapentacontane Compound 23 was dissolved in dichloromethane (c. 3 mg/ml) and was treated with dicyclohexylcarbodiimide (5 equivalents), a catalytic amount of dimethylaminopyridine, and compound 11 to give after chromatography (silica, 10% methanol/dichloromethane) compound 24.

21) compound 6

94-N-Biotin-39,75-bis(1′-oxaheptadecane)-1-phenyl-16,19,33,36,78,81,88-heptaoxo-80,87,94-triaza-6,9,12,15,20,23,26,29,32,37,41,73,77-tridecaoxa-2,3-dithiatetranonacontane Compound 23 was treated in analogous manner to compound 24 with compound 13, dicyclohexylcarbodiimide and dimethylaminopyridine in dichloromethane, followed by chromatography to give compound 6.

PREPARATION OF LINKER MOLECULE 7

22) compound 25

21-0-Gramicidin-4,18,21-trioxo-5,8,11,14,17-pentaoxauneicosanoic acid was prepared according to method described in International Patent Application No WO90/08783.

23) compound 7

O-Gramicidin 53-phenyl-4,18,21,35,38-pentaoxo-5,8,11,14,17,22,25,28,31,34,39,42,45,48-tetradecaoxa-51,52-dithiatripentacontanoate Compound 25 (0.025 g), compound 12 (0.024 g) dicyclohexylcarbodiimide (0.08 g) and dimethylaminopyridine (0.01 g) were mixed in dry dichloromethane (3 ml) and stirred for 24 h. Excess solvent was evaporated and the residue was chromatographed (silica, dichloromethane/methanol/water/triethylamine eluent, 400:44:4:1) to give compound 7 (0.0082 g).

24) compound 26

O-Gramicidin 4,18,21-trioxo-36-phenyl-34,35-dithia-5,8,11,14,17,22,25,28,31-nonaoxahexatricontanoate Gramicidin A was treated with compound 13, dicyclohexylcarbodiimide and dimethylaminopyridine in dichloromethane to give after chromatography compound 26.

Synthesis of 7,8,29,30-Tetrahydroxy-4,11,14,23,26,33-hexaoxo-5,10,15,22,27,33-hexaoxa-18,19-dithiahexatricontanedioic acid di(2,3-ditetradecanoyloxy)propanyl ester and 2,3-Ditetradecanoyloxypropanyl 7,8-dihydroxy-17-mercapto-4,11,14-trioxo-5,10,15-trioxaheptadecanoate.

25) Compound 27

2-Ethyl-4,5-di(hydroxymethyl)-2-methyl-1,3-dioxolane

A solution of 4,5-diethoxycarbonyl-2-ethyl-2-methyl-1,3-dioxolane (13.68 g, 52.6 mmol) in dry ether (80 ml) was added dropwise over 30 min to a suspension of lithiumaluminiumhydride (2.4 g, 63.2 mmol) in dry ether (100 ml) and the mixture was refluxed under nitrogen for 2 h then stirred at room temperature overnight then refluxed for 2 further hours. On cooling, water (2.5 ml), sodium hydroxide (4N, 2.5 ml) and water (25 ml) were sequentially added cautiously down the condenser. The supernatant was decanted off and the residue was triturated with ether (2×100 ml). The combined ether layers were dried over sodium sulfate, filtered and evaporated to dryness. The residue was distilled under high vacuum (approx. 2 mm, 160 deg.) to give the title compound as a clear oil (5.41 g, 58%).

26) Compound 28

2-Ethyl-4-hydroxymethyl-2-methyl-5-(3,6-dioxo-9,10-ditetradecanoyloxy-2,7-dioxadecyl)-1,3-dioxolane To a solution of 1,2-ditetradecanoyl-3-succinoylglycerol (5.29 g, 8.6 mmol), 3-ethyl-4,5-di(hydroxymethyl)-2-methyl-1,3-dioxolane (4.478 g, 25.4 mmol) and 4-dimethylaminopyridine (catalytic amount) indichloromethane (dry, 50 ml) was added dicyclohexylcarbodiimide (1.8 g, 8.7 mmol) and the mixture was stirred overnight. The mixture was then filtered and evaporated to dryness. The residue was purified by chromatography on silica gel eluted with dichloromethane and ethylacetate/dichloromethane (1:9) to afford a major fraction of the title compound (4.778 g, 72%).

27) Compound 29
5-Phenyl-3,4-dithiapentanol

A solution of benzylthiol (1.17 ml) in dry toluene (2 ml) was added dropwise over 5 min to a suspension of N-chlorosuccinimide (1.34 g) in toluene (5 ml). The mixture was stirred for 5 min the a mixture of mercaptoethanol (700 μl) and triethylamine (1.34 ml) in toluene (3 ml) was added dropwise over 5 min. The mixture was stirred for a further 10 min the diluted to 30 ml with dichloromethane, washed with water, dried over sodium sulfate, filtered and evaporated to dryness. The residue was purified by column chromatography on silica gel eluted with dichloromethane to afford the title compound (522 mg, 25%).

28) Compound 30
4-Oxo-10-phenyl-5-oxa-8,9-dithiadecanoic acid

A mixture of 5-phenyl-3,4-dithiapentanol (832 mg, 4.15 mmol), succinic anhydride (415 mg, 4.15 mmol) and 4-dimethylaminopyridine (25 mg) in dry tetrahydrofuran (20 ml) was refluxed under nitrogen overnight. The mixture was then evaporated to dryness and used without further purification.

29) Compound 31
2-Ethyl-2-methyl-4-(3,6-dioxo-12-phenyl-2,7-dioxa-10,11-dithiadodecanyl)-5-(3,6-dioxo-9,10-ditetradecanoyloxy-,7-dioxadecyl)-1,3-dioxolane To a mixture of 2-ethyl-4-hydroxymethyl-2-methyl-5-(3,6-dioxo- 9,10-ditetradecanoyloxy-2,7-dioxadecyl)-1,3-dioxolane (3.18 g, 4.13 mmol) and 4-oxo-10-phenyl-5-oxa-8,9-dithiadecanoic acid (4.15 mmol) was added dicyclohexylcarbodiimide (975 mg, 4.75 mmol) and 4-diemethylaminopyridine (catalytic amount) and the mixture was stirred overnight under a calcium chloride drying tube then filtered, evaporated and purified by column chromatography on silica gel eluted with ethyl acetate/dichloromethane (5:95) to afford the title compound (2.8 g, 64%).

30) Compound 32
2,3-Ditetradecanoyloxypropanyl 7,8-dihydroxy-17-mercapto-4,11,14-trioxo-5,10,15-trioxaheptadecanote A solution of 2-ethyl-2-methyl-4-(3,6-dioxo-12-phenyl-2,7-dioxa-10,11-dithiadodecanyl)-5-(3,6-dioxo-9,10-ditetradecanoyloxy-2,7-dioxadecyl)-1,3-dioxolane (2.06 g) in methanol (200 ml) was refluxed with Dowex 50W-X8 beads (10 g) for 4.5 h. On cooling, the mixture was filtered, and evaporated to dryness. The residue was columned on silica gel eluted with dichloromethane/ethylacetate (3:1) to afford recovered starting material (1.826 g) and the title compound (153 mg, 69% with respect to recovered starting material).

31) Compound 5
7,8,29,30-Tetrahydroxy-4,11,14,23,26,33-hexaoxo-10,15,22,27,32-hexaoxa-18,19-dithiahexatricontanedioic acid di(2,3-ditetradecanoyloxpropanyl) ester A solution of 2,3-ditetradecanoyloxypropanyl 7,8-dihydroxy-17-mercapto-4,11,14-trioxo-5,10,15-trioxaheptadecanoate (117 mg, 0.117 mmol) in ethanol (25 ml) and water (3.5 ml) was treated with tributylphosphine (50 μl) and the mixture was stirred for 30 min then evaporated to dryness. The residue was dissolved in dichloromethane, dried over sodium sulfate, and columned on silica gel eluted with dichloromethane to remove front running tributylphosphine produces thence ethyl acetate. The later eluting fractions were combined and evaporated to dryness. A solution of the residue and triethylamine (18 μl, 0.13 mmol) in dichloromethane (10 ml) was treated dropwise with a solution of iodine (15 mg, 0.059 mmol) in dichloromethane (10 ml) until a yellow colour persisted in solution (this required 9 ml of the iodine solution). The mixture was then washed with water (20 ml). The organic layer was separated and the aqueous phase was extracted with dichloromethane (2×10 ml), the combined organic phases were dried over sodium sulfate, filtered and evaporated to dryness. The residue was chromatographed on silica gel eluted with ethyl acetate/dichloromethane (3:1) to afford the title compound (50 mg, 49%).

Synthesis of 4,18,21,48,51,65-Hexaoxo-5,8,11,14,17,22,25,28,31,38,41,44,47,52,55,58,61,64-octadecaoxa-34,35-dithiaoctahexacontanedioic acid dicholesteryl ester 32) Compound 33
3,6,9,16,19,22-Hexaoxa-12,13-dithiatetraeicosane-1,24-diol A solution of 11-mercapto-3,6,9-trioxaundecanol (388 mg, 1.84 mmol) and triethylamine (256 μl, 1.84 mmol) in dichloromethane (10 ml) was treated with iodine (234 mg, 0.921 mmol) portionwise. The mixture was stirred overnight then evaporated to dryness. The residue was taken up in ethylacetate, filtered and the filtrate was evaporated to dryness to afford the title compound (390 mg, quantitative yield), which was used without further purification.

33) Compound 34
4,31-Dioxo-5,8,11,14,21,24,27,30-oxtaoxa-17,18-dithiatetratricontanedioic acid 3,6,9,16,19,22-Hexaoxa-12,13-dithiatetraeicosane-1,24-diol (390 mg, 0.92 mmol) was dried by azeotropic distillation with toluene (10 ml) then dissolved in dry tetrahydrofuran 915 ml). Succinic anhydride (388 mg, 3.88 mmol) and 4-dimethylaminopyridine (21 mg, 0.17 mmol) were added and the mixture was heated under reflux under nitrogen for 22 h. The mixture was evaporated to dryness and the residue was purified by chromatography on silica gel eluted with dichloromethane/ethylacetate (1:1) thence ethylacetate thence ethylacetate/methanol (9:1). The fractions eluted with ethylacetate/methanol (9:1) were combined and evaporated to dryness to afford the title compound (151 mg, 26%).

34) Compound 33
Succinic acid half cholesteryl ester

Succinic anhydride (20 g, 200 mmol) was added to a solution of cholesterol (70 g, 181 mmol) in pyridine (30 ml) and dichloromethane (600 ml). The solution was then refluxed for 4.5 days. On cooling, the mixture was partitioned between dichloromethane (500 ml) and aqueous hydrochloric acid (3M, 300 ml). The organic phase was separated, dried over anhydrous sodium sulfate, filtered and evaporated to dryness. Half of the residue was recrystallised from ethanol to afford the title compound (39 g, 88%).

35) Compound 34
Succinic acid half cholesteryl ester half 11-hydroxy-3,6,9-trioxaundecyl ester A mixture of succinic acid half cholesteryl ester (1.37 g, 2.81 mmol), tetraethyleneglycol (1.1 ml, 6.37 mmol), dicyclohexylcarbodiimide (770 mg, 3.73 mmol) and 4-dimethylaminopyridine (110 mg, 0.900 mmol) in dry dichloromethane (40 ml) was stirred overnight under nitrogen. The mixture was then filtered and evaporated to dryness. The residue was chromatographed on a silica column eluted with ethyl acetate/dichloromethane (1:1) to afford the title compound (861 mg, 46%).

36) Compound 35

4,18,21,48,51,65-Hexaoxo-5,8,11,14,17,22,25,28,31,38,41,44,47,52,55,58,61,64-oxtadecaoxa-34,35-dithiaoctahexacontanedioic acid dicholesteryl ester A solution of 4,31-Dioxo-5,8,11,14,21,24,27,30-octaoxa-17,18-dithiatetratricontanedioic acid (150 mg, 0.242 mmol) and succinic acid half cholesteryl ester half 11-hydroxy-3,6,9-trioxaundecyl ester (594 mg, 0.881 mg), dicyclohexylcarbodiimide (142 mg, 0.688 mmol) and 4-dimethylaminopyridine (34 mg, 0.28 mmol) in dry dichloromethane (20 ml) was stirred under nitrogen overnight. The mixture was then filtered and purified by column chromatography on silica gel eluted with dichloromethane/ethylacetate (1:1) thence ethylacetate to afford the title compound (222 mg, 48%).

Example 2

Assembly of the Sensor Membrane

Figure 8:
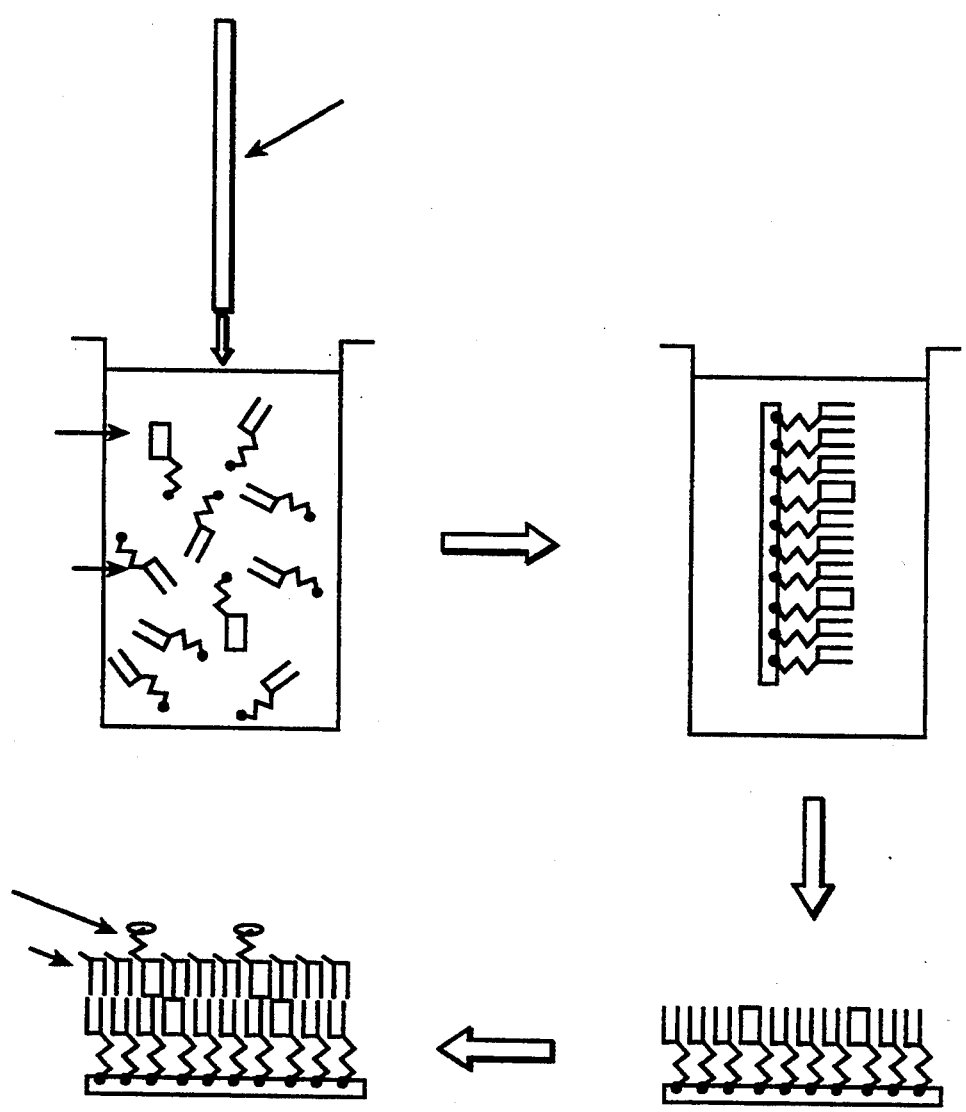
FIG. 8 shows the assembly of a sensor membrane.

The assembly of a sensor membrane using the linker molecules described in this disclosure may be accomplished following the protocol illustrated in FIG. 8. Step A: The self assembled monolayer of the linker molecules is formed according to a modification of the method taught by Bain et al (J. Am. Chem. Soc. 1989, 111, 321–325). Briefly, gold is evaporated or sputtered onto a suitable substrate such as glass, silicon or plastic in a suitable pattern to give electrode (12). The electrode (12) is then immersed in a solution containing linker molecules (11), some of which include ionophores (13) and the linker molecules chemisorb onto the gold surface to give a self assembled monolayer of linker molecules. The solvent for the linker molecules (11) and (13) is generally ethanol, decane, hexane, dichloromethane or other commonly available solvents provided that they do not interact with the substrate. The concentrations of linker molecules (11) and (13) in the solvent is not critical but is preferably less than 10 mM and greater than 0.01 mM. The time of adsorption of the linker molecule (11) and (13) is preferably greater than 10 minutes and less than two hours, although it appears that coverage is complete in less than 1 minute. Adsorption for longer than 10 minutes, up to 24 h, does not appear to adversely affect the performance of the linker molecules. Step B: The electrode (12) is then rinsed in a suitable solvent such as ethanol, hexane, decane or dichloromethane. Step C: The electrode is removed and dried. Step D: A mixture of lipid molecules (14) such as glycerol monooleate in decane (100 mg/ml), or glycerol monooleate in hexadecane (50 mg/ml) or glycerol monooleate (50 mg)+hexadecane (0.1 ml) in dioxane (1 ml) is then applied to the top of the electrode. This is then followed by the addition of 0.1M NaCl solution whereupon a bilayer membrane is formed with impedance characteristics that are typical for insulating lipid bilayer membranes as formed in the by black lipid membranes. The advantages of this method of assembly over any previous method are the increase in stability (both in terms of the length of time that the membranes last as well as the resistance to shock and vibration) of these membranes, the remarkable ease of production, and the ability to allow ionophores to conduct ions through the membrane into and out of the reservoir. If the above described mixtures of glycerol monooleate also contain ionophores such as gramicidin or valinomycin the bilayer membranes incorporating functioning ionophores are formed. Additionally it is also possible to inject aliquots of membrane compatible ionophores in a suitable solvent such as ethanol or methanol or saline into the bathing saline solution whereupon the membrane compatible ionophore will incorporate into the bilayer membrane in a functioning form. The ionophore conduction may be gated.

Figure 9:
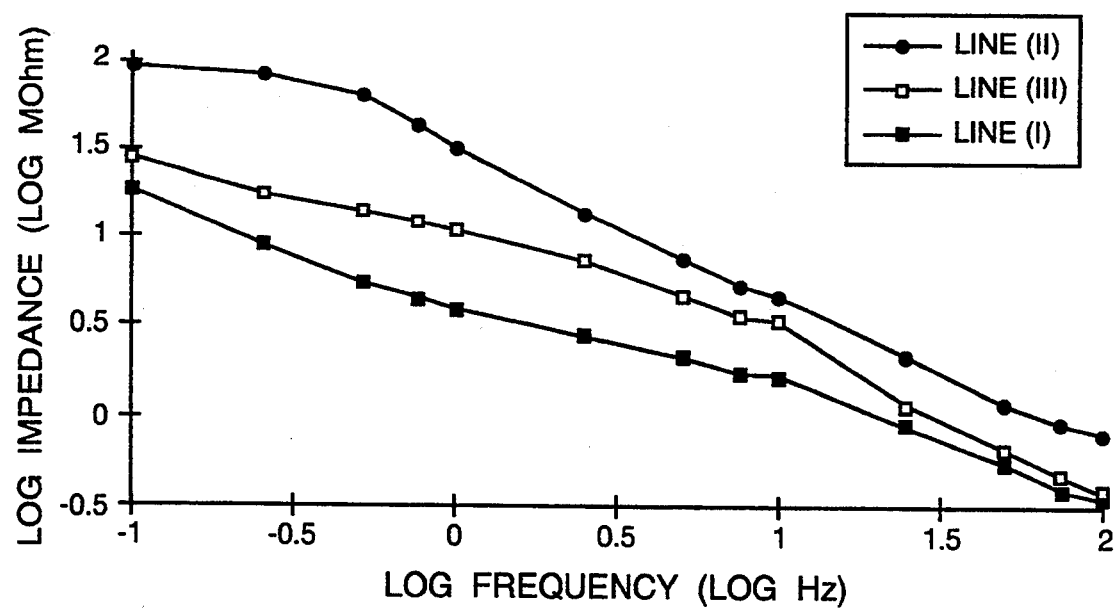
FIG. 9 is an impedance plot of log [Z] VS frequency. Line (i) is the impedance graph obtained from a bilayer membrane formed from linker compound 1 and a mixture of glycerol monooleate in decane; Line (ii) is the impedance plot of the same electrode upon addition of a biotinylated gramicidin derivative; and Line (iii) is the impedance plot of the same electrode after addition of streptravidin.

FIG. 9 shows a typical impedance plot of log[Z] vs frequency. Line (i) is the impedance graph obtained from the bilayer membrane formed from linker compound 1 and a mixture of glycerol monooleate in decane (100 mg/ml). Line (ii) is the impedance plot of the same electrode upon addition of a biotinylated gramicidin derivative showing clearly the drop in impedance on addition of the ion channel. Line (iii) is the impedance plot of the same electrode after addition of streptravidin. It is known that streptravidin causes a decrease in ion channel conduction in biotinylated gramicidin ion channels in black lipid membranes. The same gating response is clearly seen on the bilayer membranes produced using the linker molecules.

Example 3

Incorporation of valinomycin in the bilayer membrane Production of ion selective electrode for potassium ions.

Addition of valinomycin to the glycerol monooleate in decane solution (100 mg/ml, 3000:1 glycerol monooleate:valinomycin) results in a bilayer membrane on addition of this solution onto a 1 mm$^2$ gold electrode that has a monolayer of compound 1 adsorbed onto its surface. Alternatively valinomycin may be incorporated into the membrane by injection of a dilute solution of valinomycin in ethanol into the saline solution. Valinomycin is an ionophore that selectively transports potassium ions through the bilayer membrane. Other ions such as sodium are poorly transported.

Figure 10:
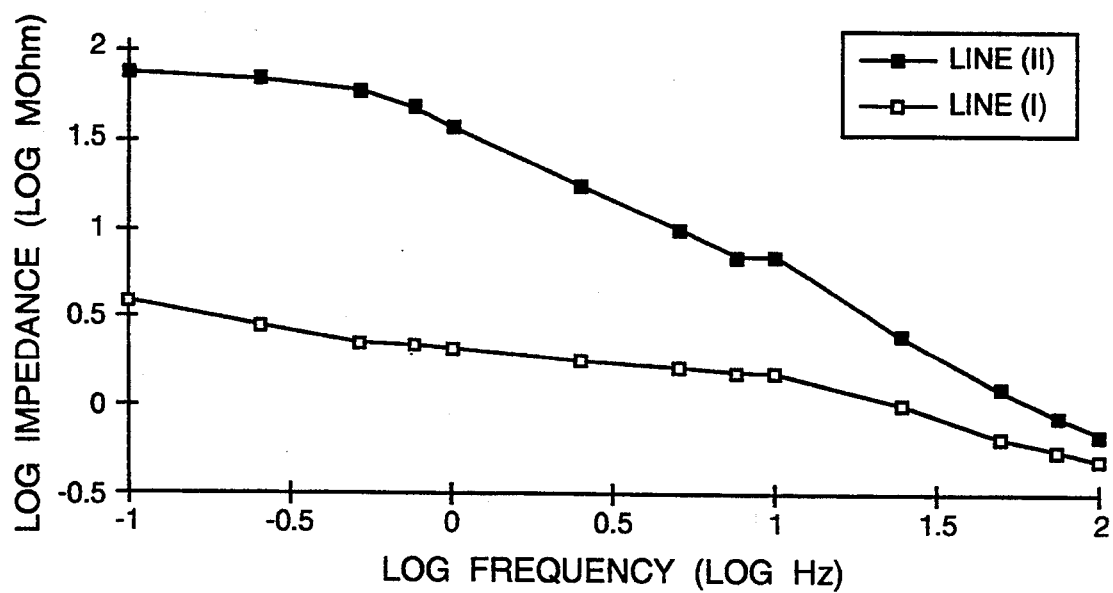
FIG. 10 shows the impedance of a bilayer membrane incorporating valinomycin in the presence 0.1M KCl (Line i) and 0.1 MNaCl (Line ii)

FIG. 10 shows the difference in the impedance in the presence of 0.1M KCl (line i)), and 0.1M NaCl (line (ii)).

Table 1 shows the impedance of the membrane at 1 Hz in the presence of 0.1M KCl and 0.1M NaCl, showing the reversible nature of the effect.

TABLE 1

| Aqueous$^a$ Phase | Na$^+$ | K$^+$ | Na$^+$ | K$^+$ | Na$^+$ | K$^+$ | Na$^+$ |
|---|---|---|---|---|---|---|---|
| log/Z/$^b$ | 7.6 | 6.15 | 7.55 | 6.0 | 7.55 | 5.9 | 7.45 |

$^a$Solutions are either 0.1M, NaCl or 0.1M K Cl solutions in water
$^b$Impedance is measured at 1 Hz and given in log (ohms)

The results obtained show that the bilayer membrane is in the fluid state as valinomycin is a carrier of ions not a channel; that the conduction of ion is through the specific ionophore and not through defect structures in the bilayer; that a single bilayer is obtained as it is unlikely that valinomycin would be transported across multilayers when injected into the saline solution from ethanol; and that a working ion selective electrode may be formed using the membrane assembly process described above. The ease of construction of the ion selective membrane may lend itself to the production of single use ion selective electrodes and multi-ion selective electrodes.

Example 4

Details of valinomycin tests for reservoir efficiency

A test was devised for determining the relative reservoir ability of the linker compounds 1-5. In this test monolayers of the linker compounds were formed by adsorbing the linker compounds from 1 mM solutions in ethanol onto freshly evaporated 1 mm2 gold electrodes. A solution of glycerol monooleate in decane (100 mg/ml, 3000:1 glycerol monooleate:valinomycin) was added, followed by 0.1M NaCl solution. The impedance of the bilayer in 0.1M NaCl and 0.1M KCl was determined at 1 Hz. The relative values of the difference of the impedance in 0.1M KCl vs. 0.1 MNa1l were taken as indication of the relative reservoir capacity of the linker compounds. The value of the impedance in 0.1M NaCl was also used as a check to insure that insulating bilayers had been formed. Table 2 shows the result of the study. Independent measurements were taken on a number of electrodes for each linker compound. As can be seen the reservoir ability can be ranked compound 1 = compound 2 > compound 5 > compound 3 > = compound 4 > > dodecylthiol.

TABLE 2

| Compound Number | log $|Z|^a$ 0.1M NaCl | log $|Z|^a$ 0.1M KCl | $\Delta$log$|Z|$ |
|---|---|---|---|
| 1 | 7.6 | 6.5 | 1.0 |
| 2 | 7.6 | 6.45 | 1.15 |
| 3 | 7.7 | 7.2 | 0.5 |
| 4 | 7.7 | 7.05 | 0.65 |
| 5 | 7.7 | 6.85 | 0.85 |
| Dodecyl thiol | 7.3 | 7.2 | 0.1 |

$^a$measured in 1 Hz given in units of log (ohms)

The reservoir ability of the linker compounds 1–5 depends on the length of the hydrophilic region on the molecule, that is linker molecules 1 and 2 which have hydrophilic regions approximately 40 Å long possess greater reservoir ability than similar compounds 3 and 4 which possess hydrophilic regions that are only approximately 20 Å long. Compound 5 which possesses a hydrophilic region of only approximately 20 Å length is however a better reservoir than compounds 3 and 4 presumably due to its increased hydrophilic character. To indicate the essential nature of the hydrophilic reservoir region of the linker molecules it is shown that a bilayer consisting of an adsorbed first layer of dodecyl thiol (a molecule that does not contain a hydrophilic reservoir region) and a second layer of the above glycerol monooleate/valinomycin gave rise to only very limited ion conduction through the bilayer.

Example 6

Details of production of coadsorbed gramicidin electrode.

A 10:1 mixture of biotinylated gramicidin and linker gramicidin (compound 7) was dissolved in trifluoroethanol. The trifluoroethanol was evaporated on a rotary evaporator. Ethanol was added to the gramicidin mixture and evaporated two times. The residue was then dissolved in 10% ethanol/dichloromethane and left for 24 h. An aliquot of this solution containing heterodimeric biotinylated gramicidin/linker gramicidin 7 as well as homodimeric biotinylated gramicidin and homodimeric gramicidin 7 was then added to a 1 mM solution of compound 1 so as to give a final ratio of 1000:1 of compound 1 to heterodimeric biotinylated gramicidin/linker gramicidin 7. Evaporated 1 mm² gold electrodes were then added to the solution and a monolayer of compound 1 and the gramicidin dimers was adsorbed. After the requisite period of time (minutes to hours) the electrode was removed and washed in 10% ethanol/dichloromethane to remove non-chemisorbed homodimeric biotinylated gramicidin. Addition of a second lipid layer using the glycerol monooleate solutions described in Example 3 a stable bilayer containing conducting gramicidin molecules was obtained. These bilayers had an average impedance of log 6.75 ohms at 1 Hz. Bilayers formed in an identical manner but without any gramicidin in the absorbing solution have an average impedance of log 7.45 ohms at 1 Hz. Bilayers containing only biotinylated gramicidin but no longer linked gramicidin (compound 7) in the adsorbing solution have an average impedance of log 7.5 ohms at 1 Hz, after rinsing the monolayer with 10% ethanol/dichloromethane in order to remove non-specifically bound gramicidin from the monolayer. If the absorbed monolayer is washed with a gramicidin disrupting solvent such as trifluoroethanol, trifluoroethanol/ethanol or dimethylsulfoxide the insulating film is formed on addition of glycerol monooleate as only the ion channel in the bottom layer remains. These bilayers have an average impedance of log 7.5 ohms at 1 Hz. Thus functioning ion channels can be incorporated into the bilayer through a coadsorption process.

It was also found that when membranes were prepared as described in Example 3 using glycerol monooleate in decane solutions in order to form the second layer, and incorporating gramicidin molecules into the bilayer, the gramicidin ion conduction through the bilayer membrane was dependent on the concentration of small neutral organic molecules such as ethanol in the saline bathing solution. For example the impedance of a typical electrode/bilayer membrane assembly at 1 Hz in 0.1M NaCl was log 7.3 ohm. On subsequently exchanging the saline with 5% methanol in 0.1M NaCl the impedance dropped to log 7.2 omh, 5% ethanol in 0.1M NaCl the impedance dropped to log 7.0 ohm, 5% dioxane in 0.1M NaCl the impedance dropped to 6.8 ohm. The effect was reversible and demonstrates the possibility of utilising the ability of analytes to influence the morphology and other physical characteristic of the membrane and hence the conduction properties of ionophores within the membrane in order to measure the presence of such analytes by the present membrane systems.

Example 7

Details of production of bilayer membrane biosensor using trifluoroethanol to achieve an improved gating response.

A 1 mm² evaporated gold on glass electrode was formed as described in Example 3. The fresh gold electrode was placed in a solution containing linker molecule 1 (0.1 mM in decane) for a period of one hour. The electrode was rinsed in decane to remove excess adsorbing solution, dried and heated at 60° C. for one hour in trifluoroethanol or left in a solution of trifluoroethanol for one week at room temperature. The electrode was removed, dried and a 1 μl of a solution containing glycerol monooleate (50 mg) in dioxane (1 ml), 2% hexadecane and biotinylated gramicidin (in a ratio of glycerol monooleate to biotinylated gramicidin of 10000:1) was added, followed by 0.1M NaCl. After exchanging the saline solution streptavidin was added as previously described (PCT WO90/08783). It was found that magnitude of the gating response was improved over electrodes that had not been subjected to the trifluoroethanol heat treatment. That is the impedance at 1 Hz for trifluoroethanol heat treated electrodes increased from 2 Mohms to 7 Mohms on addition of streptavidin, whereas the impedance at 1 Hz for electrodes without the trifluoroethanol heat treatment only rose from 1 Mohm to 2.5 Mohm.

It is also believed that provision of an ionic reservoir between the electrode and the membrane may have use in the construction of electrodes for implantation in the human body. It is envisaged that upon the electrode receiving a specified signal (e.g. the binding of a particular analyte to the membrane or the application of a DC voltage for voltage gated ion channels), that the ions present in the space between the electrode and the membrane may be released into the tissues surrounding the implanted electrode. These ions would then stimulate this tissue in a manner similar to an electric current being passed along the electrode. Following the delivery of the ions present in the reservoir, the reservoir would be refilled with ions in order that the electrode would be in a position to provide a subsequent required stimulus.

It will be appreciated by persons skilled in the art that numerous variations and /or modifications may be made to the invention as shown in the specific embodiments without departing from the spirit or scope of the invention as broadly described. The present embodiments are, therefore, to be considered in all respects as illustrative and not restrictive.

We claim:

1. An electrode membrane combination comprising an electrode and a membrane comprising a closely packed array of amphiphilic molecules and a plurality of ionophores, the membrane is connected to the electrode by means of a linker molecule(s) in a manner such that a hydrophilic space is provided between the membrane and the electrode, the space allows the flux of ions through the ionophores, the linker molecule comprising within the same molecule a hydrophobic region attached to or embedded in the membrane, an attachment region attached to the electrode and a hydrophilic region intermediate said hydrophobic and attachment regions and spanning said space between the membrane and the electrode, wherein the hydrophobic region is selected from the group consisting of dioleyl glutamate, di(X) glutamate where X is an alkyl chain between 12-20 carbon atoms in length selected from the group consisting of, glycerol didodecanoate, glycerol ditetradecanoate, glycerol dihexadecanoate, glycerol dioctadecanoate, glycerol dioleate, archaebacterial lipid, synthetic membranes spanning archaebacterial lipid mimics and membrane compatible ion channels; the attachment region is selected from the group consisting of thiol, disulphide, sulphide, thione, xanthate, phosphine, isonitrile and silyl groups, and the hydrophilic region of the linker molecule is selected from the group consisting of an oligo/ethylene oxide group consisting of 4 to 20 ethylene oxide units or 1–4 sub-units of tetraethylene glycol attached to succinic acid or 1 to 4 succinic acid/1 to 4 diesterified, 1,2,3,4-butanetetraol subunits.

2. An electrode membrane combination as claimed in claim 1 in which the distance between the membrane and the electrode is in the range 10 to 1000 Å.

3. An electrode membrane combination as claimed in claim 1 in which the space between the membrane and the electrode is in the range 15–100 Å.

4. An electrode membrane combination as claimed in claim 1 in which the hydrophobic region of the linker molecule constitutes at least a proportion of the amphiphilic molecules making up the membrane.

5. An electrode membrane combination as claimed in claim 1 in which the hydrophobic region of the linker molecule contains polymerisable groups.

6. An electrode membrane combination as claimed in claim 1 in which the hydrophobic region is gramicidin.

7. An electrode membrane combination as claimed in claim 1 in which the linker molecule comprises a benzyl disulphide attachment region, a hydrophilic region composed, in sequence of tetraethylene glycol, succinic, tetraethylene glycol and succinic acid subgroups and a hydrophobic region of dioleylglutamate.

8. An electrode membrane combination as claimed in claim 1 in which the linker molecule comprises a symmetrical disulphide attachment region, a hydrophilic region composed, in sequence of tetraethylene glycol, succinic acid, tetraethylene glycol and succinic acid subgroups and a hydrophobic region composed of cholesterol.

9. An electrode membrane combination as claimed in claim 1 in which the linker molecule comprises a symmetrical disulphide attachment region, a hydrophilic region composed, in sequence, of tetraethylene glycol and succinic acid subgroups and a hydrophobic region composed of 1,2-glycerol ditetradecanoate.

10. An electrode membrane combination as claimed in claim 1 in which the linker molecule comprises a symmetrical disulphide attachment region, a hydrophilic region comprising, in sequence, of tetraethylene glycol and succinic acid subgroups and a hydrophobic region composed of dioleylglutamate.

11. An electrode membrane combination as claimed in claim 1 in which the linker molecule comprises a thiol or disulphide attachment region, a hydrophilic region composed, in sequence, of mercaptoethanol, succinic acid, 1,4-diesterified 1,2,3,4-butanetetraol and succinic acid subunits and a hydrophobic region of 1,2-glycerol ditetradecanoate.

12. An electrode membrane combination as claimed in claim 1 in which the linker molecule comprises a benzyl disulphide attachment region, a hydrophilic region composed, in sequence, of tetraethylene glycol, succinic acid, tetraethylene glycol, succinic acid, and a hydrophobic region of 1,1'-dotriacontamethylenebis(2-hexadecyl-sn-glycerol and a head group consisting of glycine, 1,6-amino caproic acid and biotin.

13. An electrode membrane combination as claimed in claim 1 in which the linker molecule comprises a benzyl disulfide attachment region, a hydrophilic region composed, in sequence, of tetraethylene glycol, succinic acid, tetraethylene glycol, succinic acid, tetraethylene glycol, succinic acid and a hydrophobic region of gramicidin.

14. An electrode membrane combination as claimed in claim 1 in which the ionophores is gramicidin.

15. An electrode membrane combination as claimed in claim 1 in which the ionophores are gated such that in the presence of an analyte the conductance of the membrane is altered.

16. A method of assaying for the presence of an analyte in a sample comprising contacting the electrode membrane combination as claimed in claim 15 in which the ionophores are gated with the sample and measuring the conductivity.

17. A linker molecule for use in attaching a membrane to an electrode and providing a space between the membrane and the electrode, the linker molecule comprising, within the same molecule:

(i) a hydrophobic region selected from the group consisting of dioleyl glutamate, di(X) glutamate where X is an alkyl chain between 12–20 carbon atoms in length, selected from the group consisting of glycerol didodecanoate, glycerol ditetradecanoate, glycerol dihexadecanoate, glycerol dioctadecanoate, glycerol dioleate, archaebacterial lipid, synthetic membranes spanning archaebacterial lipid mimics and membrane compatible ion channels;

(ii) a hydrophilic region selected from the group consisting of an oligo/ethylene oxide group consisting of 4 to 20 ethylene oxide units or 1–4 sub-units of tetraethylene glycol attached to succinic acid or 1 to 4 succinic acid/1 to 4 diesterified, 1,2,3,4-butanetetraol subunits;

(iii) an attachment region selected from the group consisting of thiol, disulphide, sulphide, thione, xanthate, phosphine, isonitrile and silyl groups.

18. A linker molecule as claimed in claim 17 in which the hydrophobic region is gramicidin.

19. A linker molecule as claimed in claim 17 in which the linker molecule comprises a benzyl disulphide attachment region, a hydrophilic region composed, in sequence of tetraethylene glycol, succinic, tetraethylene glycol and succinic acid subgroups and a hydrophobic region of dioleylglutamate.

20. A linker molecule as claimed in claim 17 in which the linker molecule comprises a symmetrical disulphide attachment region, a hydrophilic region composed, in sequence of tetraethylene glycol, succinic acid, tetraethylene glycol and succinic acid subgroups and a hydrophobic region composed of cholesterol.

21. A linker molecule as claimed in claim 17 in which the linker molecule comprises a symmetrical disulphide attachment region, a hydrophilic region composed, in sequence, of tetraethylene glycol and succinic acid subgroups and a hydrophobic region composed of 1,2-glycerol ditetradecanoate.

22. A linker molecule as claimed in claim 17 in which the linker molecule comprises a symmetrical disulphide attachment region, a hydrophilic region comprising, in sequence, of tetraethylene glycol and succinic acid subgroups and a hydrophobic region composed of dioleylglutamate.

23. A linker molecule as claimed in claim 17 in which the linker molecule comprises a thiol or disulphide attachment region, a hydrophilic region composed, in sequence, of mercaptoethanol, succinic acid, 1,4-diesterified 1,2,3,4-butanetetraol and succinic acid subunits and a hydrophobic region of 1,2-glycerol ditetradecanoate.

24. A linker molecule as claimed in claim 17 in which the linker molecule comprises a benzyl disulphide attachment region, a hydrophilic region composed, in sequence, of tetraethylene glycol, succinic acid, tetraethylene glycols, succinic acid, and a hydrophobic region of 1,1′dotriacontamethylenebis(2-hexadecyl-sn-glycerol and a head group consisting of glycine, 1,6-amino caproic acid and biotin;

25. A linker molecule as claimed in claim 17 in which the linker molecule comprises a benzyl disulfide attachment region, a hydrophilic region composed, in sequence, of tetraethylene glycol, succinic acid, tetraethylene glycol, succinic acid, tetraethylene glycol, succinic acid and a hydrophobic region of gramicidin.

26. An ion selective electrode comprising an electrode and a membrane comprising a closely packed array of amphiphilic molecules and a plurality of ionophores selected from the group consisting of valinomycin, crown ether analogues and ion selective ion channels, the membrane is connected to the electrode by means of a linker molecule(s) in a manner such that a hydrophilic space is provided between the membrane and the electrode, the space allows the flux of ions through the ionophores, the linker molecule comprising within the same molecule a hydrophobic region which constitutes at least a proportion of the amphiphilic molecules making up the membrane or is attached to or is embedded in the membrane, an attachment region attached to the electrode and a hydrophilic region intermediate said hydrophobic and attachment regions and spanning said space between the membrane and the electrode, wherein the hydrophobic region is selected from the group consisting of dioleyl glutamate, di(X) glutamate where X is an alkyl chain between 12–20 carbon atoms in length, selected from the group consisting of glycerol didodecanoate, glycerol ditetradecanoate, glycerol dihexadecanoate, glycerol dioctadecanoate, glyceroldioleate, archaebacterial lipid, synthetic membranes spanning archaebacterial lipid mimics and membrane compatible ion channels; the attachment region is selected from the group consisting of thiol, disulphide, sulphide, thione, xanthate, phosphine, isonitrile and silyl groups, and the hydrophilic region of the linker molecule being selected from the group consisting of an oligo/ethylene oxide group consisting of 4 to 20 ethylene oxide units or 1–4 sub-units of tetraethylene glycol attached to succinic acid, or 1 to 4 succinic acid/1 to 4 diesterified, 1,2,3,4,-butanetetraol subunits.

27. A method of producing an electrode membrane combination comprising:

(1) forming a solution containing linker molecules comprising attachment regions, hydrophilic regions and hydrophobic regions which either self-assemble to form a membrane monolayer including a plurality of ionophores or which are attached to or which are embedded in a membrane monolayer composed of self-assembling amphiphilic molecules and a plurality of ionophores;

(2) contacting the electrode with the solution, the composition of the electrode and the attachment regions being selected such that the attachment regions chemisorb to the electrode;

(3) rinsing the coated electrode; and (4) soaking the coated electrode in trifluoroethanol or similar solution for about one week or treating said coated electrode at 60° C. for one hour in a solution selected from the group consisting of trifluoroethanol, trifluoroethanol/ethanol, and dimethyl sulfoxide.

28. A method as claimed in claim 27 in which a second membrane layer is assembled onto the coated electrode by contacting the coated electrode with a solution of lipid containing a $C_8$–$C_{16}$ alkane or squalene in a carrier solvent which allows partitioning of the alkane/lipid and which is water soluble.

29. A method as claimed in claim 28 in which the alkane is selected from the group consisting of N-decane, hexadecane and squalene.

* * * * *